US009758469B2

(12) United States Patent
Garrett et al.

(10) Patent No.: US 9,758,469 B2
(45) Date of Patent: *Sep. 12, 2017

(54) PROCESS FOR THE PREPARATION OF 2-SUBSTITUTED-1,4-BENZENEDIAMINES AND SALTS THEREOF

(71) Applicant: Noxell Corporation, Hunt Valley, MD (US)

(72) Inventors: Garry Steven Garrett, West Chester, OH (US); Heike Gertrud Abel, Eiterfeld (DE); Armin Osan, Bebra (DE); John Michael Gardlik, Lebanon, OH (US); Bryan Patrick Murphy, Loveland, OH (US); Markus Speckbacher, Mettenheim (DE); Ingo Reinhold Weber, Basel (CH)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,178

(22) Filed: Oct. 29, 2015

(65) Prior Publication Data

US 2016/0122285 A1 May 5, 2016

Related U.S. Application Data

(60) Provisional application No. 62/074,952, filed on Nov. 4, 2014, provisional application No. 62/074,945, filed on Nov. 4, 2014.

(51) Int. Cl.
| *C07C 213/02* | (2006.01) |
| *C07C 245/20* | (2006.01) |
| *C07C 245/24* | (2006.01) |
| *C07C 245/08* | (2006.01) |

(52) U.S. Cl.
CPC .......... *C07C 213/02* (2013.01); *C07C 245/08* (2013.01); *C07C 245/20* (2013.01); *C07C 245/24* (2013.01)

(58) Field of Classification Search
None
See application file for complete search history.

(56) References Cited

U.S. PATENT DOCUMENTS

| 2,273,564 | A | 2/1942 | Dickey et al. |
|---|---|---|---|
| 2,528,378 | A | 10/1950 | Mannheimer |
| 2,781,354 | A | 2/1957 | Mannheimer |
| 4,976,742 | A | 12/1990 | Rose et al. |
| 4,997,451 | A | 3/1991 | Clausen et al. |
| 5,662,890 | A | 9/1997 | Punto et al. |
| 6,503,282 | B1 | 1/2003 | Braun |
| 6,648,923 | B1 | 11/2003 | Goettel et al. |
| 7,591,860 | B2 | 9/2009 | Sabelle et al. |
| 7,611,545 | B2 | 11/2009 | Guerin et al. |
| 7,985,266 | B2 | 7/2011 | Zhang et al. |
| 7,988,740 | B2 | 8/2011 | Zhang et al. |
| 8,444,709 | B2 | 5/2013 | Lim et al. |
| 8,444,710 | B2 | 5/2013 | Lim et al. |
| 8,444,711 | B2 | 5/2013 | Lim et al. |
| 8,444,712 | B2 | 5/2013 | Lim et al. |
| 8,444,713 | B2 | 5/2013 | Lim et al. |
| 8,444,714 | B2 | 5/2013 | Lim et al. |
| 8,460,397 | B2 | 6/2013 | Lim et al. |
| 2003/0041392 | A1* | 3/2003 | Goettel .................. A61K 8/411 8/405 |
| 2004/0018163 | A1 | 1/2004 | Yu |
| 2006/0021152 | A1 | 2/2006 | Tsujino |
| 2008/0160620 | A1 | 7/2008 | Eccleston |
| 2009/0081143 | A1 | 3/2009 | Mammone et al. |
| 2010/0031453 | A1 | 2/2010 | Greaves et al. |
| 2010/0113311 | A1 | 5/2010 | Eccleston |
| 2011/0110990 | A1 | 5/2011 | Yu |
| 2012/0078016 | A1 | 3/2012 | Gardlik et al. |
| 2012/0130128 | A1 | 5/2012 | Göttel et al. |
| 2012/0142969 | A1 | 6/2012 | Gardlik et al. |
| 2013/0081647 | A1 | 4/2013 | Vohra et al. |
| 2013/0149358 | A1 | 6/2013 | Colaco et al. |
| 2016/0122284 | A1 | 5/2016 | Abel et al. |
| 2016/0122286 | A1 | 5/2016 | Abel et al. |

FOREIGN PATENT DOCUMENTS

| CA | 2576189 A1 | 6/2007 |
|---|---|---|
| CN | 104744272 | 7/2015 |
| DE | 20107481 U1 | 7/2001 |
| DE | 102008061864 A1 | 10/2010 |
| EP | 0052511 | 5/1982 |
| EP | 1358866 A2 | 11/2003 |
| EP | 1166749 B1 | 10/2005 |
| EP | 1765267 B1 | 1/2010 |
| FR | 2946648 A1 | 12/2010 |
| FR | 2945726 B1 | 6/2011 |
| FR | 2945731 B1 | 6/2011 |
| FR | 2945732 B1 | 6/2011 |
| FR | 2945734 B1 | 6/2011 |
| FR | 2945735 B1 | 6/2011 |
| FR | 2945736 B1 | 6/2011 |

(Continued)

OTHER PUBLICATIONS

International Search Report and Written Opinion, PCT/US2016/031088, date of mailing Jul. 14, 2016.
De Nino, A. et al.: "Synthesis of Deuterium-Labeled Azo Dyes of the Sudan Family", Synthesis, vol. 2008, No. 3, Jan. 10, 2008 (Jan. 10, 2008), pp. 459-463, XP55239996, ISSN: 0039-7881, DOI:1O.1055/S-20O8-1O32O36 Scheme 6; p. 461, p. 462; compounds (23),(24).

(Continued)

*Primary Examiner* — Clinton Brooks
(74) *Attorney, Agent, or Firm* — Schwegman Lundberg & Woessner, P.A.

(57) ABSTRACT

A process for the preparation of 2-substituted-1,4-benzenediamines, a cosmetically acceptable salt thereof, or mixture thereof. The process according to the present invention is a particularly cost effective process in that it avoids sophisticated chemical steps which requires special equipment or expensive catalysts and in that it comprises a recycling step of one of the starting materials, namely the 2-substituted aniline.

20 Claims, No Drawings

(56) References Cited

FOREIGN PATENT DOCUMENTS

| | | | |
|---|---|---|---|
| FR | 2945737 B1 | 6/2011 | |
| FR | 2945740 B1 | 6/2011 | |
| FR | 2945741 B1 | 6/2011 | |
| FR | 2945744 B1 | 6/2011 | |
| FR | 2946647 B1 | 6/2011 | |
| FR | 2945738 B1 | 7/2011 | |
| FR | 2945739 B1 | 7/2011 | |
| FR | 2945756 B1 | 8/2011 | |
| FR | 2945727 B1 | 8/2012 | |
| FR | 2945733 B1 | 8/2012 | |
| FR | 2945742 B1 | 8/2012 | |
| FR | 2945743 B1 | 9/2012 | |
| FR | 2945728 B1 | 10/2012 | |
| FR | 2945729 B1 | 10/2012 | |
| FR | 2945730 B1 | 10/2012 | |
| WO | WO2008124178 A1 | 10/2008 | |
| WO | WO-2010/133573 A2 | 11/2010 | |
| WO | WO-2010/133575 A2 | 11/2010 | |
| WO | WO-2010/133639 A1 | 11/2010 | |
| WO | WO-2010/133640 A2 | 11/2010 | |
| WO | WO-2010/133803 A1 | 11/2010 | |
| WO | WO-2010/133804 A2 | 11/2010 | |
| WO | WO-2010/133805 A1 | 11/2010 | |
| WO | WO-2010/139878 A2 | 12/2010 | |
| WO | WO-2010/142776 A1 | 12/2010 | |
| WO | WO-2010/142777 A1 | 12/2010 | |
| WO | WO-2012/044758 A1 | 4/2012 | |
| WO | WO-2016/073274 A1 | 5/2016 | |
| WO | WO-2016/073276 A1 | 5/2016 | |
| WO | WO-2016/073277 A1 | 5/2016 | |

OTHER PUBLICATIONS

Rajaganesh, R. et al.: "Synthesis and Properties of Amphiphilic Photoresponsive Gelators for Aromatic Solvents", Organic Letters, vol. 14, No. 3, Jan. 17, 2012 (Jan. 17, 2012), pp. 748-751. XP55239807, ISSN: 1523-7060, DOI: 10.1021/o1203294v, Scheme 1; p. 749, col. 1; compounds (la-f).

Rajaganesh. R. et al.: "Synthesis and Properties of Amphiphilic Photoresponsive Gelators for Aromatic Solvents, Supporting Information", Organic Letters, vol. 14, No. 3, Jan. 17, 2012 (Jan. 17, 2012). pp. S1-S46, XP55240O22, ISSN: 1523-7060. DOI: 10.1021/o1203294v, Scheme 2.1; pp. S3-S4.

Gowda, S. et al.: "Reductive cleavage of azo compounds catalysed by comnercial zinc dust and hydrazinium monoformate as a new hydrogen donor for heterogeneous catalytic transfer hydrogenation", Journal of Chemical Research—Synopses, vol. 8, 2002, pp. 384-385. XPO09187898, ISSN: 0308-2342, Scheme 1; p. 384, last entry; p. 385; table 1.

Mitrovic, J.; Decolorization of the textile azo dye Reactive Orange 16 by the UV/H2O2 process; Journal of Serbian Chemical Society 77 (4) 465-481 (2012) JSCS-4283.

Jadhav, N.; Validated Visible Spectrophotometric Estimation of Para-Phenylendiamine, a Carcinogenic Ingrediaent in Henna Hair Dyes; Journal of Pharmacy & Technology; ISSN: 0975-766X.

Ozgur, M.; A Rapid Spectrophotometric Method to Resolve a Binary Mixture of Food Colorants (Riboflavine and Sunset Yellow); Turk J Chem 28 (2004), 325-333.

Golob, V.; VIS absorption spectrophotometry of disperse dyes; Dyes and Pigments 40 (1999) 211-217.

Dhavile, S.M.; Determination of trace phosphorus in zirconium-niobium alloy and Zircaloy by UV-vis spectrophotometry; Talanta 76 (2008) 134-137.

Ni, Y; Simultaneous Spectrophotometric Determination of Ternary Mixtures of Tartrazine, Sunset Yellow, and Ponceau 4R by H-Point Standard Addition Method; Analytical Letters; ISSN: 0003-2719.

"U.S. Appl. No. 14/926,135, Non Final Office Action dated Sep. 8, 2016", 6 pgs.

"U.S. Appl. No. 14/926,135, Notice of Allowance dated Mar. 9, 2017", 7 pgs.

"U.S. Appl. No. 14/926,135, Response filed Feb. 8, 2017 to Non Final Office Action dated Sep. 8, 2016", 8 pgs.

"U.S. Appl. No. 14/926,163, Non Final Office Action dated Sep. 9, 2016", 7 pgs.

"U.S. Appl. No. 14/926,163, Notice of Allowance dated Mar. 10, 2017", 7 pgs.

"U.S. Appl. No. 14/926,163, Response filed Feb. 8, 2017 to Non Final Office Action dated Sep. 9, 2016", 11 pgs.

"Chapter 6 Polysaccharides", In: Polymers in Nature, E. A. MacGregor and C. T. Greenwood, published by John Wiley & Sons, Chapter 6, (1980), 240-328.

Encyclopedia of Chemical Technology, Kirk-Othmer, Third Edition, vol. 3, (1982), 896-900.

Encyclopedia of Chemical Technology, Kirk-Othmer, Third Edition, vol. 15, (1982), 439-458.

"International Application Serial No. PCT/US2015/058028, International Search Report dated Jan. 25, 2016", 5 pgs.

"International Application Serial No. PCT/US2015/058028, Written Opinion dated Jan. 25, 2016", 7 pgs.

"International Application Serial No. PCT/US2015/058046, International Search Report dated Jan. 25, 2016", 5 pgs.

"International Application Serial No. PCT/US2015/058046, Written Opinion dated Jan. 25, 2016", 7 pgs.

"International Application Serial No. PCT/US2015/058047, International Search Report dated Jan. 25, 2016", 4 pgs.

"International Application Serial No. PCT/US2015/058047, Written Opinion dated Jan. 25, 2016", 8 pgs.

Abiraj, Keelara, et al., "Palladium-catalyzed simple and efficient hydrogenative cleavage of azo compounds using recyclable polymer-supported formate", Canadian Journal of Chemistry, 83(5), (2005), 517-519.

Goebel, Carsten, et al., "Introduction of a methoxymethyl side chain intopphenylenediamine attenuates its sensitizing potency and reduces the risk of allergy induction", Toxicology and Applied Pharmacology. 274(3), (2013), 480-487.

Griffiths, John, et al., "Steric Effects in 4-Dimethylamino-azobenzenes and Their Protonated Species", Journal of Chemical Research. Miniprint, Scientific Reviews, (1981), 3722-3739.

Hallas, Geoffrey, "The Effects of Terminal Groups in 4-Amino-azobenzene and Disperse Dyes Related Thereto", Journal of the Society of Dyers and Colourists, 95(8), (Aug. 1979), 285-294.

Horner, Leopold, et al., "Sterisch behindertes Buttergelb und cancerogene Wirkung", Chemische Berichte, vol. 89, No. 12, (1956), 2756-2759.

Jones, F., et al., "Orientation of Dyes in Liquid Crystalline Media", Journal of the Society of Dyers and Colourists, 95(10), (Oct. 1979), 352-359.

Porter, M., "6 Anionics", In: Handbook of Surfactants, published by Blackie & Son (Glasgow and London), (1991), 99-168.

Shin, Dong-Myung, et al., "Solvent-induced mechanism change in chargetransfer molecules. Inversion versus rotation paths for the Z .fwdarw. E isomerization of donor-acceptor substituted azobenzenes", Journal of the America Chemical Society, 110(15), (1988), 5206-5208.

Van Loon A., et al., "Preparation of some 4-dimethylamino-azobenzene derivatives with substituents in the 3- or in the 3-and the 5-position", Recueil, 79, (1960), 977-1001.

Whistler, Roy L, "Industrial Gums-Polysaccharides and their Derivatives", Academic Press, Inc., (1973), 341-397, 427-444 and 461-474 (49 pgs.).

\* cited by examiner

PROCESS FOR THE PREPARATION OF 2-SUBSTITUTED-1,4-BENZENEDIAMINES AND SALTS THEREOF

FIELD OF THE INVENTION

The present invention relates to a process for the preparation of 2-substituted-1,4-benzenediamines or salts thereof. These compounds can be used as couplers and/or primary intermediates in compositions for dyeing keratin fibers.

BACKGROUND OF THE INVENTION 2-substituted-1,4-benzenediamine, for example 2-methoxymethyl-1,4-benzenediamine, and cosmetically acceptable salts thereof are useful as primary intermediates in oxidative hair color.

Although the diazotization route to p-phenylenediamine (PPD) is known (EP 0052511 A1), and it has been used to manufacture PPD successfully, it is similarly well-known that, although the synthesis of 2-methyl-p-phenylenediamine has been accomplished by a diazotization route on a smaller scale (Rajaganesh, Ramanathan et al; Organic Letters, 14(3), 748-751; 2012), there has been an inability to use it as an industrial route CA 2,576,189 discloses the application of combinations of 2-methoxymethyl-1,4-benzenediamine with various couplers and primary intermediates in oxidative dyeing compositions. U.S. Pat. No. 2,273,564 discloses a process to synthesize substituted 1,4-benzenediamine compounds with a substituent on the 2 position. U.S. Pat. No. 6,648,923 B1 discloses a process to synthesize 2-methoxymethyl-1,4-benzenediamine and the salts thereof. U.S. Pat. No. 9,012,691 describes a process to prepare 2-methoxymethyl-1,4-benzenediamine and the salts thereof beginning with 5-nitroisatoic anhydride.

The previous syntheses described above to reach 2-alkoxymethyl-1,4-benzenediamines, their derivatives, and salts thereof are not completely satisfactory. Therefore, there is a need for a simple, industrially applicable, efficient, and cost effective process for the preparation of 2-substituted-1,4-benzenediamines, a cosmetically acceptable salt thereof or mixture thereof.

The inventors have surprisingly found that at least some of these needs may be met by a process according to the present invention wherein the reaction by-product (a 2-substituted aniline) can be recycled in the process by distillation, chromatography, etc.

SUMMARY OF THE INVENTION

The present invention relates to a process for the preparation of 2-substituted-1,4-benzenediamines (I), a cosmetically acceptable salt thereof, or mixture thereof comprising the steps of:
a) in situ generation of diazonium salt of formula (III) from the 2-substituted aniline of formula (II) followed by addition of the unreacted 2-substituted aniline of formula (II) to form the triazene intermediate of formula (IV):

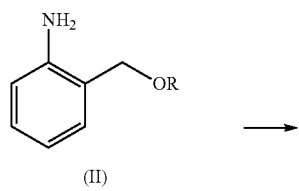

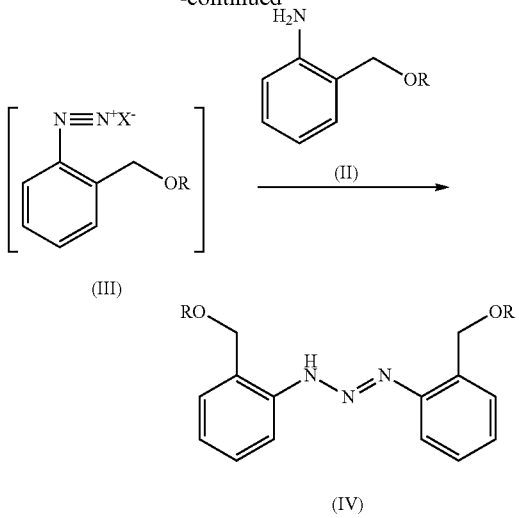

b) rearrangement of the of triazene intermediate of formula (IV) to the diazo compound of formula (V):

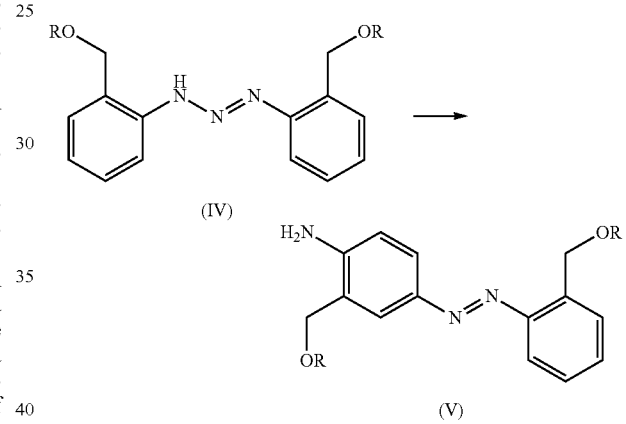

c) reduction of the diazo compound of formula (V) to obtain an equimolar amount of 2-substituted-1,4-benzenediamines (I) and the 2-substituted aniline of formula (II):

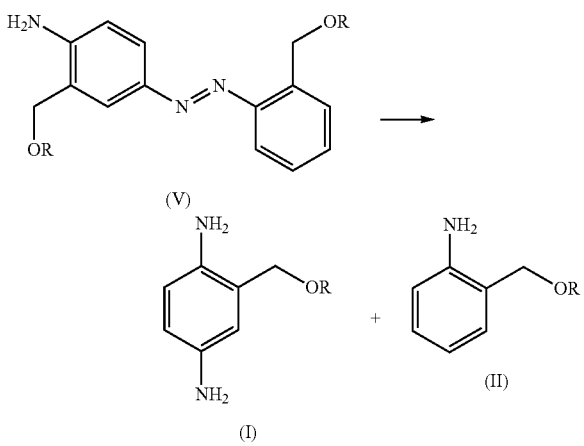

d) optionally converting 2-substituted-1,4-benzenediamines (I) into a cosmetically acceptable salt using at least one mineral or organic acid HZ:

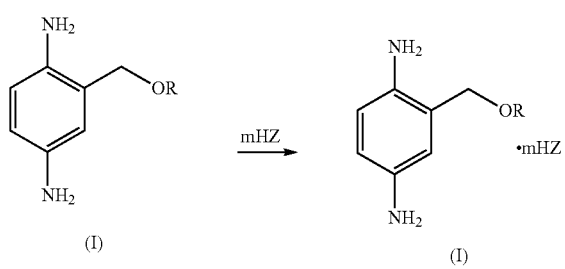

wherein R is selected from the group consisting of a hydrogen atom and a $C_1$-$C_4$ alkyl group, preferably wherein R is a methyl group;
wherein $X^-$ is a mineral or an organic anion,
wherein m=0.5, 1 or 2.

DETAILED DESCRIPTION OF THE INVENTION

The sequence of steps, including all identified intermediates, involved in the telescoping synthesis and large scale process, is now described in detail. It is to be understood that when this development refers to a particular structure, all of the reasonable additional tautomeric structures are included. In the art tautomeric structures are frequently represented by one single structure and the invention follows this general practice.

The present invention relates to a process for the preparation of 2-substituted-1,4-benzenediamines (I), a cosmetically acceptable salt thereof, or mixture thereof comprising the steps a), b) and c) as described hereinafter.

a) In Situ Generation of Diazonium Salt of Formula (III) from the 2-Substituted Aniline of Formula (II) Followed by Addition of the Unreacted 2-Substituted Aniline of Formula (II) to Form the Triazene Intermediate of Formula (IV):

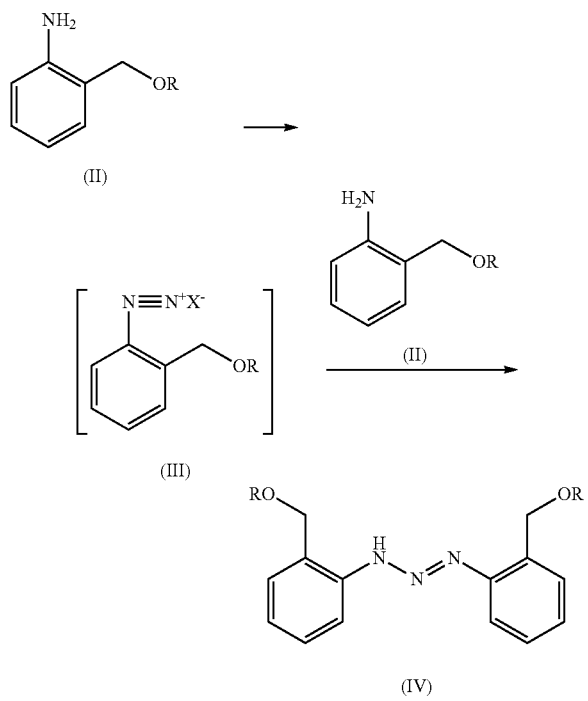

Step a) is carried out in the presence of at least one nitrosation agent in combination with at least one mineral or organic acid. The nitrosation agent may be selected from the group consisting of sodium nitrite, potassium nitrite, $N_2O_5$, nitrosyl sulphuric acid and mixtures thereof. The mineral or organic acid may be selected from the group consisting of hydrogen chloride, sulfuric acid, acetic acid and mixtures thereof.

Step a) may be carried out in the presence of at least one radical scavenger selected from the group consisting of acrylonitrile, methacrylate, urea and mixtures thereof. Radical scavengers may be used in order to avoid the formation of azotars which would negatively impact the overall yield of the triazene intermediate of formula (IV).

b) Rearrangement of the of Triazene Intermediate of Formula (IV) to the Diazo Compound of Formula (V):

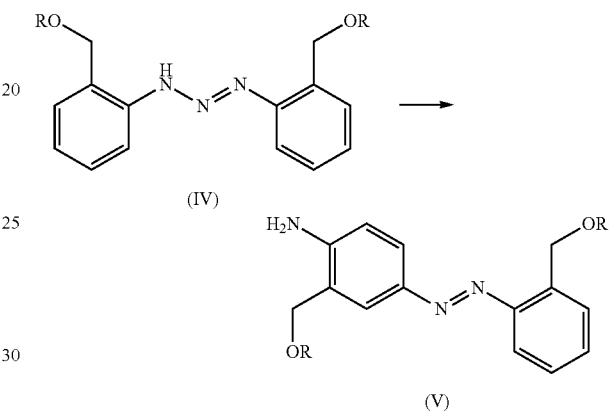

The rearrangement occurs by heating the triazene intermediate of formula (IV) in the presence of the 2-substituted aniline of formula (II).

Step a) and/or b) is carried out in the presence of at least one solvent. The solvent used in step a) and/or b) may be selected from the group consisting of pentane, cyclopentane, hexane, cyclohexane, benzene, toluene, 1,4-dioxane, chloroform, diethyl ether, dichloromethane, tetrahydrofuran, methyl-tetrahydrofuran, 1,2-dimethoxyethane, ethyl acetate, acetone, dimethylformamide, acetonitrile, dimethyl sulfoxide, glycols, n-butanol, isopropanol, n-propanol, ethanol, methanol, water, and mixtures thereof.

c) Reduction of the Diazo Compound of Formula (V) to Obtain an Equimolar Amount of 2-Substituted-1,4-Benzenediamines (I) and the 2-Substituted Aniline of Formula (II):

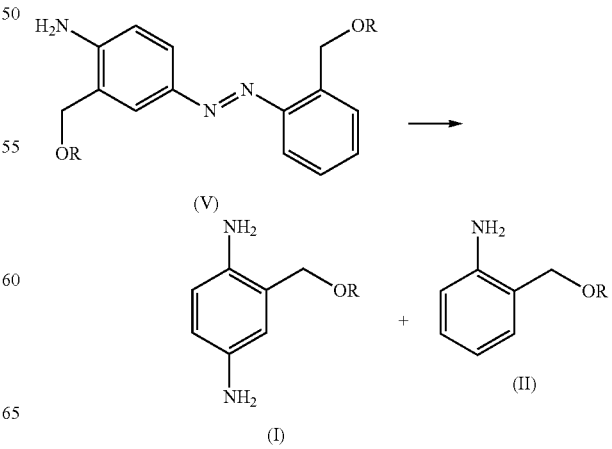

Step c) may be carried out in the presence of at least one reducing agent with at least one metal catalyst. The reducing agent may be selected from dihydrogen, hydrazine. The reducing agent may advantageously be dihydrogen. The metal catalyst may be selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, and mixtures thereof.

Step c) is carried out in the presence of at least one solvent. The solvent may be selected from the group consisting of water, petroleum ether, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol, and mixtures thereof. The solvent may advantageously be selected from the group consisting of ethyl acetate, ethanol and mixtures thereof.

In a further step d), 2-substituted-1,4-benzenediamines (I) can be converted into a cosmetically acceptable salt using at least one mineral or organic acid HZ.

By HZ is meant any mineral or organic acid having an acid proton "H". "Z" represents the rest of the molecule. For example if HZ=HCl, then Z=Cl. Another example can be if HZ=CH$_3$CO$_2$H, then Z=CH$_3$CO$_2$.

The value for "m" may be 0.5, 1, or 2, advantageously m=1.

The mineral or organic acid HZ may be selected from the group consisting of D,L-malic acid, L-malic acid, D-malic acid, hydrochloric acid, hydrobromic acid, citric acid, acetic acid, lactic acid, succinic acid, tartaric acid, phosphoric acid, or sulfuric acid and mixtures thereof.

Step d) may be carried out in the presence of at least one solvent. The solvent may be selected from the group consisting of pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof. The solvent may advantageously be selected from the group consisting of ethanol, water and mixtures thereof.

Step d) may be carried out at a temperature ranging from −20° C. to 150° C., advantageously under inert gas atmosphere at room temperature. By room temperature it is meant 20-28° C.

The process according to the present invention is a particularly cost effective process for preparing 2-substituted-1,4-benzenediamines (I), a cosmetically acceptable salt thereof, or mixture thereof since it avoids sophisticated chemical steps which requires special equipment or expensive catalysts and it comprises a recycling step of one of the starting materials, namely 2-substituted aniline of formula (II).

Surprisingly, it has been found that labile functional groups like methoxy are stable and do not lead to side reactions. Furthermore, the process according to the present invention provides materials with a low impurity level. Finally, this process is efficient in carbon, i.e. no protecting groups are required, hence waste (e.g. from protecting groups that might normally be discarded) is minimized.

The starting material of the process according to the present invention is 2-substituted aniline of formula (II). These compounds are commercially available. However, these compounds may be prepared according to different synthesis routes such as synthesis route A), B) or C) disclosed hereinafter:

A) Preparation of 2-Substituted Aniline of Formula (II) Starting from 2-Nitrobenzyl Alcohol of Formula (VI)

When R is selected from a C$_1$-C$_4$ alkyl group, the 2-substituted aniline of formula (II) may be prepared by etherification of 2-nitrobenzyl alcohol of formula (VI) to obtain 2-alkoxymethyl-nitrobenzene of formula (VII) followed by reduction of 2-alkoxymethyl-nitrobenzene of formula (VII):

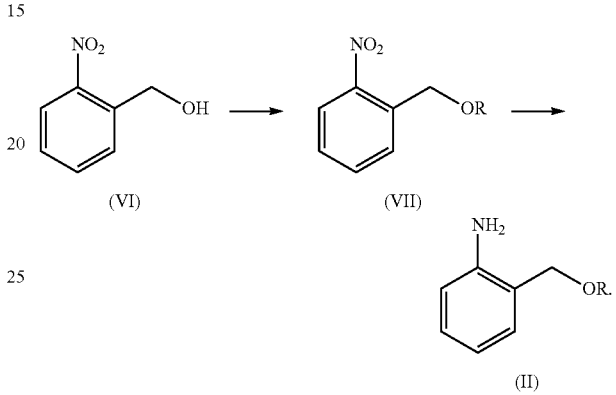

When R is a hydrogen atom, the 2-substituted aniline of formula (II) is prepared by reduction of the 2-nitrobenzyl alcohol of formula (VI):

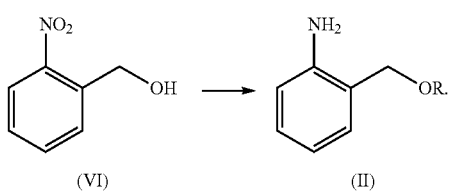

Etherification of 2-Nitrobenzyl Alcohol of Formula (VI)

The etherification may be performed by an alkylation reaction, a condensation reaction or a nucleophilic substitution.

Alkylation Reaction

The etherification may be performed by an alkylation reaction in the presence of at least one alkylating agent, at least one phase transfer catalyst, at least one solvent and/or at least one base. The reaction mixture may be homogeneous or heterogeneous, may have two or more liquid phases, and/or may have any combination of liquid and solid phases.

The alkylating agent may be selected from the group consisting of alcohols, derivatives of alcohols (i.e. methyl methanesulfonate), (C$_1$-C$_4$)—I, (C$_1$-C$_4$)—Br, (C$_1$-C$_4$)—Cl, dimethyl sulfate, and mixtures thereof. The alkylating agent may advantageously be dimethyl sulfate.

The phase transfer catalyst may be selected from the group consisting of ammonium salts selected from tetrapentylammonium bromide, tetraoctylammonium chloride, tetraoctylammonium bromide, tetrahexylammonium iodide, tetrahexylammonium chloride, tetraheptylammonium bromide, tetraethylammonium tetrafluoroborate, tetraethylammonium chloride, tetraethylammonium bromide, tetradodecylammonium tetrafluoroborate, tetradodecylammonium chloride, tetradodecylammonium bromide, tetradecyl-trimethylammonium chloride, benzyltriethyl ammonium chloride, phenyl-trimethylammonium bromide, octyl-trimethylammonium bromide, octadecyl-trimethylammonium chloride, octadecyl-trimethylammonium bromide, methyl-trioctylammonium iodide, and mixtures thereof. The phase transfer catalyst may advantageously be benzyltriethyl ammonium chloride.

The solvent may be selected from the group consisting of water, petroleum ether, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol, and mixtures thereof.

The base may be selected from the group consisting of sodium hydroxide, potassium hydroxide, ammonium hydroxide, calcium hydroxide, magnesium hydroxide, barium hydroxide, aluminum hydroxide, ferrous hydroxide, ferric hydroxide, zinc hydroxide, lithium hydroxide, sodium bicarbonate, sodium carbonate, and mixtures thereof. The base may advantageously be sodium hydroxide.

Condensation Reaction

The etherification may be performed by a condensation reaction with at least one alcohol in the presence of at least one condensation catalyst and/or at least one solvent.

The alcohol may be selected from the group consisting of methanol, ethanol, 1-propanol, 2-propanol, n-butanol and mixtures thereof.

The condensation catalyst may be selected from the group consisting of mineral acids, Lewis Acids, aluminum chloride, titanium tetra-isopropoxide, and mixtures thereof.

The solvent may be selected from the group consisting of petroleum ether, pentane, cyclopentane, hexane, cyclohexane, benzene, toluene, 1,4-dioxane, chloroform, diethyl ether, tetrahydrofuran, methyl-tetrahydrofuran, acetone, dimethylformamide, acetonitrile, dimethyl sulfoxide, n-butanol, isopropanol, n-propanol, ethanol, methanol, and mixtures thereof. The solvent may advantageously be methanol.

The condensation reaction may be carried out with at least one inert solvent diluent and/or with heating. The inert solvent diluent may be chosen to aid in the removal of water if it is capable of forming a low boiling azeotrope. In this case, the condensation reaction may be carried out at reflux using a Dean Stark trap to drain off the water as it is formed and distilled off with the azeotrope.

The condensation reaction may also be carried out in the presence of at least one dehydrating agent which may either react with or physically bind with the water, thereby removing the water from equilibrium. The dehydrating agent may be selected from the group consisting of dicyclohexylcarbodiimide, molecular sieves, magnesium sulphate, and mixtures thereof.

Nucleophilic Substitution

The etherification may also be performed by a nucleophilic substitution reaction in the presence of at least one alkoxide and/or at least one solvent.

The alkoxide may be selected from the group consisting of sodium, potassium, zinc, calcium, magnesium, tantalum, tributyltin salts of alcohols and mixtures thereof. FeSO4 may be used with an alcohol to catalyze the alkoxylation. For example, FeSO4 may be used with methanol to catalyze the methoxylation.

The solvent may be selected from the group consisting of pentane, cyclopentane, hexane, cyclohexane, benzene, toluene, 1,4-dioxane, chloroform, diethyl ether, tetrahydrofuran, methyl-tetrahydrofuran, acetone, dimethylformamide, acetonitrile, dimethyl sulfoxide, n-butanol, isopropanol, n-propanol, ethanol, methanol and mixtures thereof. The solvent may advantageously be a mixture of tetrahydrofuran and an alcohol.

Reduction of 2-Alkoxymethyl-Nitrobenzene of Formula (VII) or 2-Nitrobenzyl Alcohol of Formula (VI)

The reduction may be carried out in the presence of at least one reducing agent with at least one metal catalyst. The reducing agent may be selected from the group consisting of dihydrogen, ammonium formate, hydrazine and mixtures thereof. The reducing agent may advantageously be dihydrogen. The hydrogen pressure may be in a range from atmospheric pressure to 200 psi, alternatively from 50 psi to 60 psi.

The metal catalyst may be selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, and mixtures thereof.

The reduction may be carried out in the presence of at least one solvent. The solvent may be selected from the group consisting of water, petroleum ether, pentane, cyclopentane, hexane, cyclohexane, benzene, toluene, 1,4-dioxane, chloroform, diethyl ether, tetrahydrofuran, methyl-tetrahydrofuran, ethyl acetate, acetone, dimethylformamide, acetonitrile, n-butanol, isopropanol, n-propanol, ethanol, methanol and mixtures thereof.

B) Preparation of 2-Substituted Aniline of Formula (II) Starting from 2-Halomethyl-Nitrobenzene of Formula (VIII)

2-substituted aniline of formula (II) may be prepared by alkoxylation 2-halomethyl-nitrobenzene of formula (VIII) to obtain 2-alkoxymethyl-nitrobenzene of formula (VII) followed by reduction of the 2-alkoxymethyl-nitrobenzene of formula (VII):

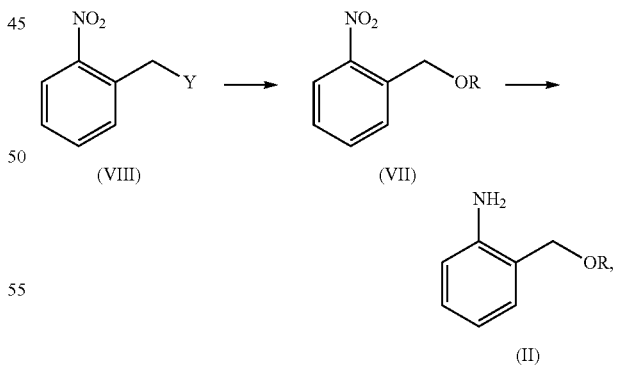

wherein Y is an halogen selected from the group consisting of bromine, chlorine, and iodine.

Alkoxylation of 2-Halomethyl-Nitrobenzene of Formula (VIII)

The alkoxylation may be carried out in the presence of at least one alkoxylating agent. The alkoxylating agent may be selected from the group consisting of alcohols, sodium alkoxides, potassium alkoxides, zinc alkoxides, calcium alkoxides, magnesium alkoxides, tantalum alkoxides, tributyltin alkoxides, salts thereof and mixtures thereof.

If the alkoxylation is a methoxylation, the methoxylating agent may be selected from the group consisting of methanol, sodium methoxide, potassium methoxide, zinc methoxide, calcium methoxide, magnesium methoxide, tantalum methoxide, tributyltin methoxide, $FeSO_4$, salts thereof and mixtures thereof.

The alkoxylation or hydroxylation may be carried out in the presence of at least one solvent. The solvent may be selected from the group consisting of pentane, cyclopentane, hexane, cyclohexane, benzene, toluene, 1,4-dioxane, chloroform, diethyl ether, tetrahydrofuran, methyl-tetrahydrofuran, acetone, dimethylformamide, acetonitrile, dimethyl sulfoxide, n-butanol, isopropanol, n-propanol, ethanol, methanol, and mixtures thereof.

Reduction of the 2-Alkoxymethyl-Nitrobenzene of Formula (VII)

The reduction may be carried out in the presence of at least one reducing agent with at least one metal catalyst. The reducing agent may be selected from dihydrogen, ammonium formate, hydrazine. The reducing agent may also be a combination of metallic elements with acids, such as zinc/acetic acid, iron/hydrochloric acid and other well-known reducing agent. The reducing agent may advantageously be dihydrogen. The hydrogen pressure may be in a range from atmospheric pressure to 200 psi, alternatively from 50 psi to 60 psi.

The catalyst may be selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, and mixtures thereof.

Examples

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

1.1 Preparation of 2-methoxymethyl-nitrobenzene (VII) Starting from 2-nitrobenzyl alcohol (VI)

2-nitrobenzyl alcohol (100 g, 0.653 mole) was partitioned between 50% NaOH (136 g, 1.7 mole) and petroleum ether (500 mL). Benzyl triethylammonium chloride (2 g) was added followed by dimethyl sulfate (106.4 g, 0.84 mole) introduced via an addition funnel (moderate rate). The mixture was stirred (mechanically) until complete. Dimethyl sulfate (10 mL) was added and the reaction was stirred for 1 hour. The excess dimethyl sulfate was quenched by the addition of ammonium formate (100 mL) and the mixture transferred to a separatory funnel. The petroleum ether phase was collected. The aqueous phase was extracted one additional time with 500 mL of petroleum ether and the combined extracts were evaporated and residual solvent removed under high vacuum. The 2-methoxymethyl-nitrobenzene was obtained (104 g, 95%) as a faint yellow oil. TLC analysis (50% EtOAc-pet ether) showed a single component of very high purity. $H^1$—NMR (600 MHz, $CDCl_3$) δ 3.55 (s, 3H), 4.85 (s, 2H), 7.43 (dd, 1H), 7.68 (d, 1H), 7.79 (d, 1H), 8.09 (d, 1H). $C^{13}$ NMR (600 MHz, $CDCl_3$) 135.4, 132.8, 128.7, 128.15, 124.8, 71.3, 59.1. IS-MS m/z 168 [MH+].

1.2 Preparation of 2-methoxymethyl-nitrobenzene (VII) Starting from 2-bromomethyl-nitrobenzene (VIII)

2-bromomethyl-nitrobenzene (25 g, 116 mmole) was dissolved in methanol (400 mL). 25% Sodium methoxide (25 g, 116 mmole) was added at room temperature. The reaction was heated to 50° C. and the reaction monitored by TLC analysis. An additional 2 g of 25% sodium methoxide was added and TLC indicated complete consumption of starting material. The methanol was evaporated and the residue suspended in dichloromethane (700 mL) and washed with water (2 times 125 mL) and saturated sodium chloride. Evaporation provided 2-methoxymethyl-nitrobenzene (19.5 g, 100%) as a faint yellow oil. TLC and NMR analyses indicated high purity. $H^1$—NMR (600 MHz, $CDCl_3$) δ 3.55 (s, 3H), 4.85 (s, 2H), 7.43 (dd, 1H), 7.68 (d, 1H), 7.79 (d, 1H), 8.09 (d, 1H). $C^{13}$ NMR (600 MHz, $CDCl_3$) 135.4, 132.8, 128.7, 128.15, 124.8, 71.3, 59.1. IS-MS m/z 168 [MH+].

2. Preparation of 2-methoxymethylaniline (II) Starting from 2-methoxymethyl-nitrobenzene (VII)

2-methoxymethyl-nitrobenzene (100 g, 0.598 mole) was added to a 2 L Parr bottle along with ethanol (600 mL) and 5% Pd/C (5 g). The mixture was hydrogenated at 50 psi for 2 hours. The reaction mixture was filtered thru a bed of Celite™ and then thru a glass microfiber filter to remove all traces of catalyst. Evaporation of the solvent provided 2-methoxymethylaniline (40 g, 97.5%) in very high purity as judged by proton NMR and TLC analysis. $H^1$—NMR (600 MHz, $CDCl_3$) 3.55 (s, 3H), 4.15 (s, 2H, $NH_2$), 4.5 (s, 2H), 6.68 (m, 2H), 7.08 (d, 1H), 7.15 (d, 1H). $C^{13}$—NMR (600 MHz, $CDCl_3$) 146.5, 130.8, 129.6, 122.2, 118.8, 115.3, 73.9, 57.8. IS-MS 105.4 (MH+, 100)

3. Preparation of 1,3-bis(2-(methoxymethyl)phenyl) triaz-1-ene (IV) Starting from 2-methoxymethylaniline (II)

2-methoxymethylaniline (5.0 g, 37.5 mmoles) was suspended in water (25 mL). Ice and concentrated HCl were added to get the temperature to 10° C. Sodium nitrite (1.26 g, 18.3 mmoles) was dissolved in 4 mL water and added to the above cold solution keeping temperature below 10° C. Sodium acetate (5.1 g, 62.2 mmoles) was dissolved in 10 mL water and added to reaction mixture. The reaction mixture was place in an ice-water bath and stirred for 2 hours at 0-5° C. The reaction mixture was extracted twice with dichloromethane (125 mL and 50 mL). The combined extracts were evaporated to provide impure product. Chromatography on silica gel provided pure 1,3-bis(2-(methoxymethyl) phenyl)triaz-1-ene (3.7 g, 71%). $H^1$—NMR (600 MHz, $CDCl_3$) 3.45 (s, 6H), 4.7 (s, 4H), 7.2 (m, 2H), 7.4 (m, 4H), 7.7 (d, 2H). $C^{13}$—NMR (600 MHz, $CDCl_3$) 172, 129, 125, 116, 71.8, 57.9. IS-MS m/z 286 [MH+] (5), 222 [M-2X $^-OCH_3]^+$, (20).

4. Preparation of 2-(methoxymethyl)-4-((2-(methoxymethyl)phenyl)diazenyl)aniline (V) Starting from 1,3-bis(2-(methoxymethyl)phenyl)triaz-1-ene (IV)

1,3-Bis(2-(methoxymethyl)phenyl)triaz-1-ene (1.0 g, 3.5 mmoles) was dissolved in dichloromethane along with 2-(methoxymethyl)aniline (3.0 g, 21.87 mmoles) and 2-(methoxymethyl)aniline hydrochloride (0.500 g, 5.8 mmoles). The mixture was refluxed for 4 hours then diluted to 125 mL dichloromethane and washed with 1N HCl (5×25 mL). Chromatography on silica gel (Combiflash) provided 2-(methoxymethyl)-4-((2-(methoxymethyl)phenyl)diazenyl)aniline (0.560 g, 56%) as a red oil. $H^1$—NMR (600 MHz, $CDCl_3$) 3.4 (s, 3H), 3.51 (s, 3H), 4.58 (s, 2H), 4.65 (s, 2H, $NH_2$), 5.05 (s, 2H), 6.78 (d, 1H), 6.38 (d, 1H), 6.4 (d, 1H), 7.61 (dd, 1H), 7.65 (dd, 1H), 7.75 (s, 1H), 7.8 (d, 1H). $C^{13}$—NMR 150.25, 149.97, 145.4, 136.6, 130.1, 128.6, 128.2, 128.17, 125.15, 121.85, 115.6, 73.9, 70.15, 58.68, 57.75

5. Preparation of 2-methoxymethyl-1,4-benzenediamines (I) Starting from 2-(methoxymethyl)-4-((2-(methoxymethyl)phenyl)diazenyl)aniline (V)

2-(methoxymethyl)-4-((2-(methoxymethyl)phenyl)diazenyl)aniline (0.75 g, 2.63 mmoles) was dissolved in methanol (10 mL). Ammonium formate (2.0 g) and activated zinc (2 g) were added and the mixture stirred at room temperature. After 1 hour, TLC analysis demonstrated complete consumption of the starting material. Chromatography on silica gel (combiflash) provided 2-methoxymethyl-1,4-benzenediamine (0.180 g, 45%) as a white solid. $H^1$—NMR (500 MHz, $CDCl_3$) δ 3.2-3.9 (m, 7H), 4.39 (s, 2H), 6.5 (s, 1H), 6.56 (s, 2H).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A process for the preparation of 2-substituted-1,4-benzenediamines (I), a cosmetically acceptable salt thereof, or mixture thereof comprising the steps of:
   a) in situ generation of diazonium salt of formula (III) from the 2-substituted aniline of formula (II) followed by addition of the unreacted 2-substituted aniline of formula (II) to form the triazene intermediate of formula (IV):

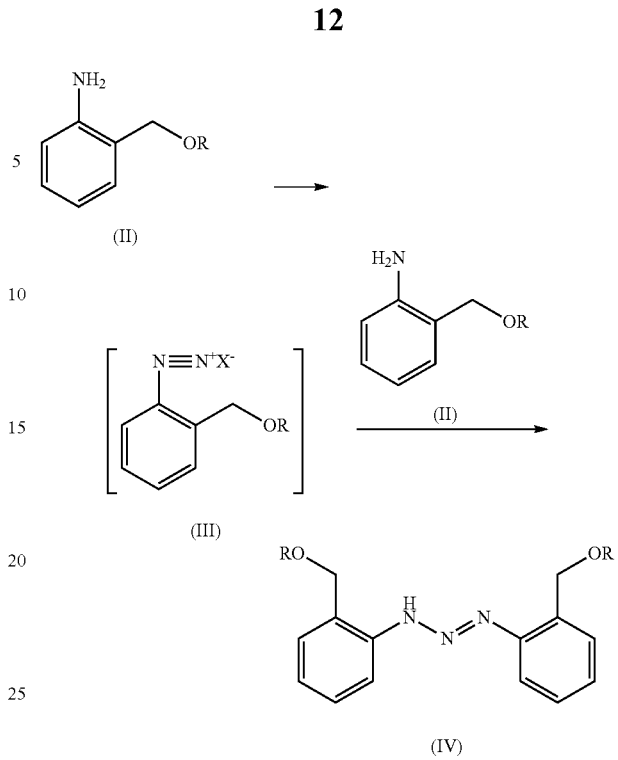

wherein R is selected from the group consisting of a hydrogen atom and a $C_1$-$C_4$ alkyl group;

b) rearrangement of the of triazene intermediate of formula (IV) to the diazo compound of formula (V):

c) reduction of the diazo compound of formula (V) to obtain an equimolar amount of 2-substituted-1,4-benzenediamines (I) and the 2-substituted aniline of formula (II):

-continued

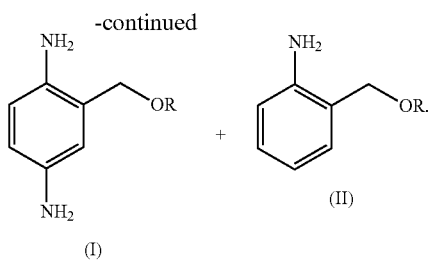

(I) + (II)

2. The process according to claim 1, wherein the process further comprises the step of converting 2-substituted-1,4-benzenediamines (1) into a cosmetically acceptable salt using at least one acid HZ:

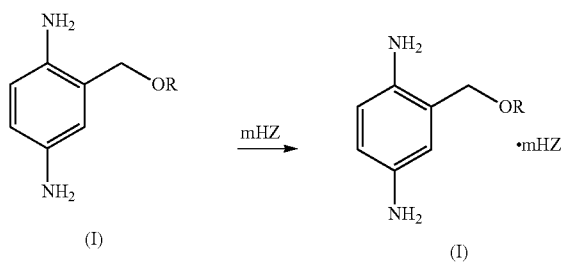

(I) → (I)

wherein R is selected from the group consisting of a hydrogen atom and a $C_1$-$C_4$ alkyl group;
wherein Z is a mineral or an organic anion,
wherein m=0.5, 1 or 2.

3. The process according to claim 2, wherein R is a methyl group.

4. The process according to claim 1, wherein step a) is carried out in the presence of at least one nitrosation agent in combination with at least one mineral or organic acid.

5. The process according to claim 4, wherein the nitrosation agent is selected from the group consisting of sodium nitrite, potassium nitrite, $N_2O_5$, nitrosyl sulphuric acid and mixtures thereof and the mineral or organic acid is selected from the group consisting of hydrogen chloride, sulfuric acid, acetic acid and mixtures thereof.

6. The process according to claim 1, wherein step a) is carried out in the presence of at least one radical scavenger selected from the group consisting of acrylonitrile, methacrylate, urea and mixtures thereof.

7. The process according to claim 1, wherein step a) or b) is carried out in the presence of at least one solvent selected from the group consisting of pentane, cyclopentane, hexane, cyclohexane, benzene, toluene, 1,4-dioxane, chloroform, diethyl ether, dichloromethane, tetrahydrofuran, methyl-tetrahydrofuran, 1,2-dimethoxyethane, ethyl acetate, acetone, dimethylformamide, acetonitrile, dimethyl sulfoxide, glycols, n-butanol, isopropanol, n-propanol, ethanol, methanol, water, and mixtures thereof.

8. The process according to claim 1, wherein step c) is carried out in the presence of at least one reducing agent with at least one metal catalyst.

9. The process according to claim 8, wherein the catalyst is selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, and mixtures thereof.

10. The process according to claim 1, wherein step c) is carried out in the presence of at least one solvent selected from the group consisting of water, petroleum ether, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol, and mixtures thereof.

11. The process according to claim 1, wherein the acid HZ used in step d) is selected from the group consisting of D,L-malic acid, L-malic acid, D-malic acid, hydrochloric acid, hydrobromic acid, citric acid, acetic acid, lactic acid, succinic acid, tartaric acid, phosphoric acid, or sulfuric acid and mixtures thereof.

12. The process according to claim 1, wherein step d) is carried out in the presence of at least one solvent selected from the group consisting of pentane, cyclopentane, hexane, cyclo hexane, benzene, toluene, 1,4-dioxane, chloroform, diethyl ether, dichloromethane, tetrahydrofuran, methyl-tetrahydrofuran, ethyl acetate; acetone, dimethylformamide, acetonitrile, dimethyl sulfoxide, n-butanol, isopropanol, n-propanol, ethanol, methanol and mixtures thereof.

13. The process according to claim 1, wherein step d) is carried out in the presence of at least one solvent selected from the group consisting of ethanol, water and mixture thereof.

14. The process according to claim 1, wherein:
i) when R is selected from a $C_1$-$C_4$ alkyl group, the 2-substituted aniline of formula (II) is prepared by etherification of 2-nitrobenzyl alcohol of formula (VI) to obtain 2-alkoxymethyl-nitrobenzene of formula (VII) followed by reduction of 2-alkoxymethyl-nitrobenzene of formula (VII):

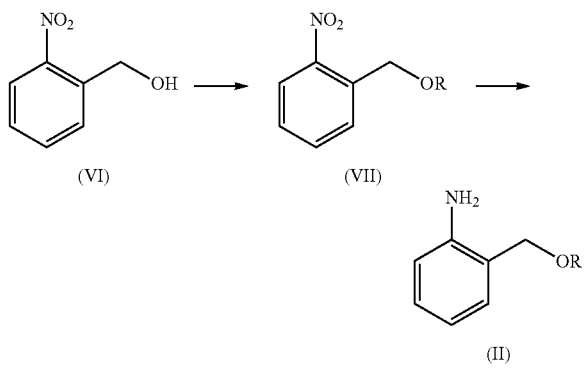

(VI) → (VII) → (II)

or
ii) when R is a hydrogen atom, the 2-substituted aniline of formula I) is prepared by reduction of the 2-nitrobenzyl alcohol of formula (VI)

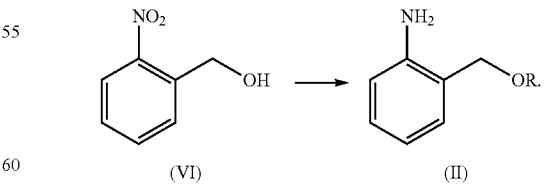

(VI) → (II)

15. The process according to claim 14, wherein the etherification is performed by an alkylation reaction, a condensation reaction or a nucleophilic substitution.

16. The process according to claim 1, wherein the 2-substituted aniline of formula (II) is prepared by alkoxylation of 2-halomethyl-nitrobenzene of formula (VIII) to obtain 2-alkoxymethyl-nitrobenzene of formula (VII) followed by reduction of the 2-alkoxymethyl-nitrobenzene of formula (VII):

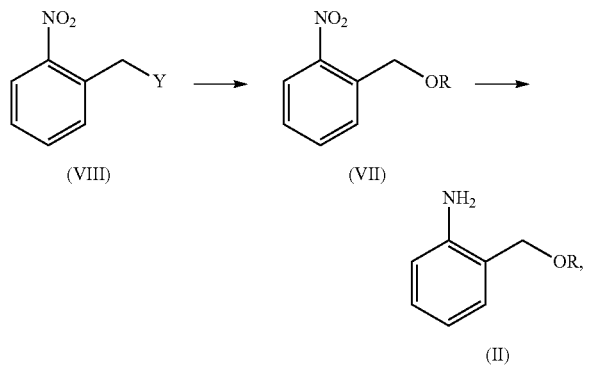

wherein Y is an halogen selected from the group consisting of bromine, chlorine and iodine.

17. The process according to claim 16, wherein the alkoxylating agent used for the alkoxylation is selected from the group consisting of alcohols, sodium alkoxides, potassium alkoxides, zinc alkoxides, calcium alkoxides, magnesium alkoxides, tantalum alkoxides, tributyltin alkoxides, salts thereof and mixtures thereof.

18. The process according to claim 16, wherein the alkoxylation is carried out using a solvent selected from the group consisting of pentane, cyclopentane, hexane, cyclohexane, benzene, toluene, 1,4-dioxane, chloroform, diethyl ether, tetrahydrofuran, methyl-tetrahydrofuran, acetone, dimethylformamide, acetonitrile, dimethyl sulfoxide, n-butanol, isopropanol, n-propanol, ethanol, methanol, and mixtures thereof.

19. The process according to claim 16, wherein the reduction is carried out in the presence of at least one reducing agent with at least one metal catalyst.

20. The process according to claim 19, wherein the catalyst is selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, and mixtures thereof.

* * * * *